United States Patent
Hayashi et al.

(10) Patent No.: US 11,016,078 B2
(45) Date of Patent: *May 25, 2021

(54) ELECTROCHEMICAL MEASUREMENT METHOD, ELECTROCHEMICAL MEASUREMENT DEVICE AND TRANSDUCER

(71) Applicants: JAPAN AVIATION ELECTRONICS INDUSTRY, LIMITED, Tokyo (JP); TOHOKU UNIVERSITY, Miyagi (JP)

(72) Inventors: Hiroyuki Hayashi, Tokyo (JP); Ryota Kunikata, Tokyo (JP); Atsushi Suda, Tokyo (JP); Kosuke Ino, Miyagi (JP); Kumi Inoue, Miyagi (JP); Tomokazu Matsue, Miyagi (JP)

(73) Assignees: JAPAN AVIATION ELECTRONICS INDUSTRY, LIMITED, Tokyo (JP); TOHOKU UNIVERSITY, Miyagi (JP)

( * ) Notice: Subject to any disclaimer, the term of this patent is extended or adjusted under 35 U.S.C. 154(b) by 301 days.

This patent is subject to a terminal disclaimer.

(21) Appl. No.: 15/776,195

(22) PCT Filed: Oct. 11, 2016

(86) PCT No.: PCT/JP2016/080102
§ 371 (c)(1),
(2) Date: May 15, 2018

(87) PCT Pub. No.: WO2017/086059
PCT Pub. Date: May 26, 2017

(65) Prior Publication Data
US 2020/0173978 A1 Jun. 4, 2020

(30) Foreign Application Priority Data
Nov. 20, 2015 (JP) ............................. JP2015-228042

(51) Int. Cl.
*G01N 27/327* (2006.01)
*G01N 33/483* (2006.01)
*G01N 27/416* (2006.01)

(52) U.S. Cl.
CPC ..... *G01N 33/4836* (2013.01); *G01N 27/4161* (2013.01); *G01N 27/327* (2013.01)

(58) Field of Classification Search
CPC ............... G01N 27/327; G01N 27/403; G01N 33/4836; C12Q 1/02; C12Q 1/025; C12Q 1/04
See application file for complete search history.

(56) References Cited

U.S. PATENT DOCUMENTS 8,097,134 B2   1/2012  Li
10,732,137 B2* 8/2020  Hayashi ............... G01N 27/416
(Continued)

FOREIGN PATENT DOCUMENTS

CN  1886652 A   12/2006
EP  2840389 A1   2/2015
(Continued)

OTHER PUBLICATIONS

Ino et al., "Electrochemical device with interdigitated ring array electrodes for investigating the relationship between cardiomyocyte differentiation from embryonic stem cells and alkaline phosphatase activity", Electochemistry, Sep. 5, 2013, pp. 682-687.
(Continued)

*Primary Examiner* — Alexander S Noguerola
(74) *Attorney, Agent, or Firm* — Greenblum & Bernstein, P.L.C.

(57) ABSTRACT

An electrochemical measurement method is provided in which a working electrode that causes an oxidation-reduction reaction with a measurement target and a counter electrode connected to the working electrode are provided in
(Continued)

an electrolytic solution containing the measurement target, and a measuring voltage is applied between the working electrode and the counter electrode to measure a current that flows between the working electrode and the counter electrode in proportion to the amount of the measurement target, wherein an eliminating electrode is provided in the electrolytic solution, and the method performs: eliminating the measurement target by applying an eliminating voltage, which has the same polarity as the measuring voltage, between the eliminating electrode and the counter electrode to oxidize or reduce the measurement target; diffusing a new measurement target; and measuring the current by applying the measuring voltage between the working electrode and the counter electrode.

16 Claims, 13 Drawing Sheets

(56) References Cited

U.S. PATENT DOCUMENTS

| | | |
|---|---|---|
| 2002/0123048 A1 | 9/2002 | Gau |
| 2007/0062822 A1 | 3/2007 | Fujiwara et al. |
| 2010/0243479 A1 | 9/2010 | Choi et al. |
| 2014/0158554 A1 | 6/2014 | Choi et al. |
| 2017/0336384 A1 | 11/2017 | Ino et al. |

FOREIGN PATENT DOCUMENTS

| | | |
|---|---|---|
| EP | 2840398 A1 | 2/2015 |
| EP | 3128000 A1 | 2/2017 |
| JP | 2003-532090 A | 10/2003 |
| JP | 2005-148058 A | 6/2005 |
| JP | 2010-227089 A | 10/2010 |
| JP | 2013-092437 A | 5/2013 |
| WO | 2015/151395 A1 | 10/2015 |

OTHER PUBLICATIONS

Sen et al., "LSI-based amperometric sensor for real-time monitoring of embryoid bodies", Biosensors and Bioelectronics, 48 (2013), pp. 12-18.

Kanno et al., "Simulation analysis of positional relationship between embryoid bodies and sensors on an LSI-based amperometric device for electrochemical imaging of alkaline phosphatase activity", Analytical Sciences, Jul. 10, 2015, pp. 715-719.

U.S. Appl. No. 16/063,570 to Ryota Kunikata et al., which was filed on Jun. 18, 2018.

Office Action issued in Japan family member Patent Appl. No. 2015-228042, dated Dec. 20, 2016, along with an English translation thereof.

Office Action issued in Taiwan family member Patent Appl. No. 105133440, dated Nov. 24, 2017, along with an English translation thereof.

International Search Report issued in PCT Patent Appl. No. PCT/JP2016/080102, dated Dec. 27, 2016.

Kanno et al., "A Local Redox Cycling-Based Electrochemical Chip Device with Nanocavities for Multi-Electrochemical Evaluation of Embryoid Bodies", Lab on a Chip, Oct. 6, 2015, pp. 4404-4414.

Office Action issued in Singapore family member Patent Appl. No. 11201804099R, dated Jul. 31, 2019.

Office Action issued in China family member Patent Appl. No. 201680066920.0, dated Aug. 1, 2019, along with an English translation thereof.

Kanno et al., "A local redox cycling-based electrochemical chip device with nanocavities for multi-electrochemical evaluation of embryoid bodies", Lab on a Chip, Jan. 1, 2015, pp. 4404-4407.

Office Action issued in European Patent Office (EPO) family member Patent Appl. No. 16866061.1, dated Jan. 8, 2019.

Office Action issued in European Patent Office (EPO family member Patent Appl. No. 16866061.1, dated Dec. 12, 2019.

* cited by examiner

ELECTROCHEMICAL MEASUREMENT METHOD, ELECTROCHEMICAL MEASUREMENT DEVICE AND TRANSDUCER

TECHNICAL FIELD

The present invention relates to an electrochemical measurement method, an electrochemical measurement device, and a transducer used for electrochemical measurement for measuring chemical substances (chemical reaction products) derived from cells, cell aggregates, pieces of tissue and other biological specimens, and non-biological specimens containing biologically-relevant substances (which are collectively simply referred to as "biological specimens" hereafter).

BACKGROUND ART

Quantifying a substance produced through a chemical reaction that occurs in biological specimens such as cells, cell aggregates, and pieces of tissue is a technique required for viability assay, functional assay and the like of biological specimens in fields such as medical and drug-discovery. One method for quantifying a chemical reaction product released from a biological specimen is electrochemical measurement. For example, the progress of stem cell differentiation is monitored using electrochemical measurement in Non-patent literature 1.

Electrochemical measurement is a method in which an oxidization or reduction reaction, by removing electrons from a measurement target or supplying electrons to the measurement target through an electrode, is caused on the measurement target in an electrolytic solution in which two or more electrodes connected to an external power source are inserted and, at the same time, a current flowing between the electrodes is measured to determine whether an oxidation-reduction reaction has occurred, that is, to detect the presence or absence of the measurement target.

A typical electrochemical measurement device includes a working electrode which supplies and receives electrons to and from a measurement target to cause an oxidation-reduction reaction, a counter electrode which is connected to the working electrode through an external power source and compensates for electron transfer occurring at the working electrode, an electrolytic solution which enables transfer of electrons through ions in a measurement system and makes the measurement system a closed circuit, and a reference electrode for providing a reference for voltage.

In Non-patent literature 1, alkaline phosphatase (ALP), which is an undifferentiation marker which exists in the cell membranes of embryonic stem (ES) cells is indirectly measured by electrochemical measurement on an embryoid body (EB) which is an aggregate of ES cells produced from ES cells of a mouse.

The reaction in which a stem cell whose function is yet to be determined changes to a somatic cell whose function is determined is commonly referred to as differentiation and a substance that indicates that differentiation has not occurred is referred to as an undifferentiation marker.

ALP is an undifferentiation marker and also has the property of hydrolyzing a phosphoric ester compound under alkaline conditions. For example, ALP acts as an enzyme in a reaction that changes p-aminophenol phosphate (PAPP), which is a phosphoric ester compound, into p-aminophenol (PAP). PAP produced by the enzymatic reaction is a substance that is electrochemically active and is oxidized to p-quinone imine (PQI) by application of a voltage to a working electrode using the reference electrode as a reference. Specifically, the presence of ALP is detected as a current value in electrochemical measurement through two reactions, namely an enzymatic reaction and an oxidation-reduction reaction.

In Non-patent literature 1, a multielectrode amperometric device in which 20×20=400 working electrodes each having ϕ40-μm are provided in an array with a pitch of 250 μm is used for measurement. The device two-dimensionally images reactions in biological specimens of several to several hundred micrometers over time by using electrode current values acquired from the 400 electrodes.

PRIOR ART LITERATURE

Non-Patent Literature

Non-patent literature 1: M. Sen, et al., "Biosensors and Bioelectronics", 2013, Vol. 48, p. 12-18

SUMMARY OF THE INVENTION

Problems to be Solved by the Invention

The measurement in Non-patent literature 1 is performed in the following process, which is illustrated in FIG. 1 where the horizontal axis represents time.

Mouse EB is introduced in an electrolytic solution containing $4.7 \times 10^{-3}$ mol/L of PAPP.

Enzymatic reaction starts immediately after the introduction and PAPP changes to PAP by ALP present in cell membranes.

PAP diffuses from the surface of the EB to regions near the electrodes and reaches the surfaces of the electrodes.

A voltage is applied to the electrodes after the diffusion is stabilized.

PAP changes to PQI.

Interelectrode current values are acquired.

In FIG. 1, the time A from the start of the enzymatic reaction after the introduction of the EB to the application of the voltage is set by taking into consideration the time required for a start of diffusion of PAP from the surface of the EB and the PAP concentration distribution in the electrolytic solution to stabilize, and the time B from the voltage application to the current value acquisition is provided by taking into consideration the time required for changes in the PAP concentration distribution near the electrodes to be stabilized by a oxidation-reduction reaction which occurs on the electrodes.

In measurement of ALP activity in EB that follows such a process, uncertainty of the measurement can occur.

For example, in the case where a multiple EBs are concurrently measured, the EBs contact PAPP at different timings when the EBs are placed on the electrodes in an array with a pipette or the like in multiple batches. Accordingly, the time A from the start of an enzymatic reaction to voltage application differs from EB to EB and the PAP concentration distributions around the EBs and current values vary even if all of the EBs have activities (PAP release rates per unit time) similar to one another. That is, both of a difference due to different levels of ALP activities of the EBs and a difference due to the lengths of the time A from the start of the enzymatic reaction to the voltage application appear in measured current values.

Even if multiple EBs are concurrently introduced in a PAPP solution, it may be difficult to compare a result of measurement on a group of EBs performed at a certain time with a result of measurement on the group of EBs performed at a different time because of reasons such as a difference in liquid fluctuations due to, for example, a manner in which an operator has introduced the EBs.

An object of the present invention is to provide an electrochemical measurement method and an electrochemical measurement device that are capable of making measurement conditions uniform among iterations of measurement and among samples on which measurement is performed at a time, thus enabling accurate measurement and accurate comparison between results of measurement in the iterations and results of measurement performed on the samples at a time, and a transducer used for electrochemical measurement by the electrochemical measurement method and device.

Means to Solve the Problems

The present invention provides an electrochemical measurement method in which a working electrode that supplies and receives electrons to and from a measurement target to cause an oxidation-reduction reaction and a counter electrode connected to the working electrode through an external power source are provided in an electrolytic solution containing the measurement target, and a measuring voltage is applied between the working electrode and the counter electrode to measure a current that flows between the working electrode and the counter electrode in proportion to the amount of the measurement target. The electrochemical measurement method provides a measurement target eliminating electrode in the electrolytic solution and performs a measurement target eliminating step of eliminating the measurement target by applying an eliminating voltage, which has the same polarity as the measuring voltage, between the measurement target eliminating electrode and the counter electrode to oxidize or reduce the measurement target, a measurement target diffusion step of diffusing a new measurement target after stopping the application of the eliminating voltage, and an electrochemical measurement step of measuring the current by applying the measuring voltage between the working electrode and the counter electrode after the new measurement target is diffused.

The present invention also provides an electrochemical measurement device including an electrolytic solution well to contain an electrolytic solution and a biological specimen that produces a measurement target in the electrolytic solution, a working electrode that is provided in the electrolytic solution and causes an oxidation-reduction reaction by supplying and receiving electrons to and from the measurement target, a counter electrode provided in the electrolytic solution, measuring voltage applying means for applying a measuring voltage between the working electrode and the counter electrode, and current measuring means for measuring a current that flows between the working electrode and the counter electrode in proportion to the amount of the measurement target while the measuring voltage is being applied, wherein a measurement target eliminating electrode that causes an oxidation-reduction reaction by supplying and receiving electrons to and from the measurement target is provided in the electrolytic solution well, and the electrochemical measurement device comprises eliminating voltage applying means for applying an eliminating voltage, which has the same polarity as the measuring voltage, between the measurement target eliminating electrode and the counter electrode while the measuring voltage is not applied between the working electrode and the counter electrode.

Further, the present invention provides a transducer in which an electrolytic solution well that can contain an electrolytic solution and a biological specimen immersed in the electrolytic solution is mounted on an LSI chip, the transducer being used for electrochemical measurement of a measurement target generated from the biological specimen, wherein first electrodes arranged in an array and provided on the LSI chip and second electrodes provided on the LSI chip in such a way that each of the second electrodes is positioned around each of the first electrodes are positioned in a sensor region defined on a bottom surface of the electrolytic solution well.

Effects of the Invention

The electrochemical measurement method according to the present invention eliminates a measurement target produced and diffused in an electrolytic solution, then produces and diffuses a measurement target again and performs measurement, and an electrochemical measurement device according to the present invention is capable of such measurement. Therefore, the electrochemical measurement method and the electrochemical measurement device according to the present invention are capable of making conditions for production and diffusion of measurement targets uniform, i.e. capable of making measurement conditions uniform, thereby enabling accurate measurement.

Consequently, results of measurement can be accurately compared with one another among iterations of the measurement and among samples (biological specimens) on which measurement is performed at a time.

Further, the transducer according to the present invention is suitable for use in such electrochemical measurement.

DETAILED DESCRIPTION OF THE EMBODIMENTS

Figure 1:
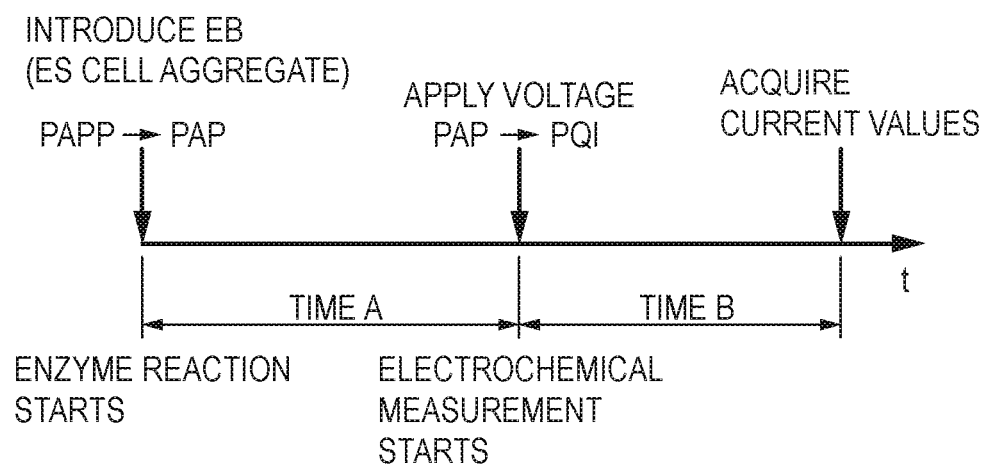
FIG. 1 is a chart illustrating an example of a conventional measurement process of electrochemical measurement.

Results of a numerical analysis by a finite element method will be described first using measurement of ALP activity of mouse EBs as an example. COMSOL Multiphysics Ver. 4.4 was used as numerical analysis software. Analytical model forms and boundary conditions will be described below.

<Analytical Model Forms>

An analytic space of 2.3 mm×2.3 mm×1.3 mm was provided and electrodes (working electrodes) each having $\phi$40-$\mu$m are disposed in an array on the bottom surface of the analytic space. The thickness of the electrodes was specified to be 1 nm as a sufficiently negligible value for the setting.

An origin was set at the center of the bottom surface of the analytic space of 2.3 mm×2.3 mm, 8×8=64 electrodes were placed with a pitch of 250 $\mu$m so that the center of the entire electrode array coincides with the center of the bottom surface of the analytic space. A spherical object that models an EB of $\phi$300 $\mu$m was placed so that the center of the EB was above the electrode in the fourth row and the fifth column near the center of the electrode array. The distance between the spherical object and the electrode located immediately below the spherical object was chosen to be 3 $\mu$m by taking into consideration the ease of cutting an analytic mesh.

<Boundary Conditions>

A substrate pAPP with a concentration of 4.7×10$^{-3}$ mol/L was set in the analytic space as the initial value of the concentration in the space and the four walls and ceiling of the analytic space were set as open boundaries where the concentration outside the analytic space was 4.7×10$^{-3}$ mol/L. The surface of the EB (the surface of the spherical object) was set as a boundary through which PAP was released in accordance with the Michaelis-Menten equation (1) given below, depending on the concentration of PAPP near the surface. This was an enzymatic reaction model.

[Equation 1]

$$v = \frac{V_{max}[S]}{K_m + [S]} \quad (1)$$

v: PAP release rate [mol/s]

[S]: Substrate PAPP concentration (4.7×10$^{-3}$ mol/L)

$V_{max}$: Rate of reaction at the maximum PAPP concentration (3.33×10$^{-12}$ mol/s)

$K_m$: Michaelis-Menten constant (1.7×10$^{-3}$ mol/L)

In order to express an oxidation-reduction reaction of PAP, the PAP concentration was set to 0 on the electrodes during voltage application and a current value was calculated from the PAP concentration gradient. The current value is proportional to the concentration gradient in the direction perpendicular to the electrodes and follows equation (2).

[Equation 2]

$$i = nFD\frac{dC(x, y, z)}{dz} \quad (2)$$

i: Current density [A/m$^2$] at an arbitrary point (x, y, z) on the electrodes

C: PAP concentration at the arbitrary point (x, y, z) [mol]

z: Component perpendicular to the electrodes x, y: Components horizontal to the electrodes F: Faraday constant (96485 C/mol)

D: Diffusion coefficient of redox species PAP (6.47×10$^{-10}$ m$^2$/s)

n: The number of reaction electrons (n=2)

Note that in order to evaluate the influence of the PAP concentration distribution in a visually clear manner, current values of seven electrodes (seven electrodes along the Y axis) in the same column on which the EB was placed among the 64 electrodes were used for evaluation.

Figure 2:
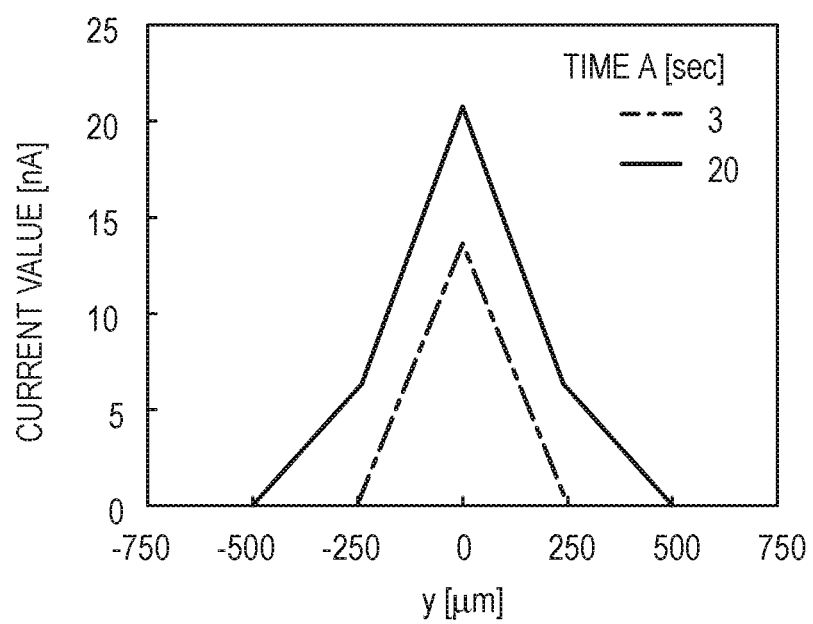
FIG. 2 is a graph illustrating a difference in calculated current values that arises due to a difference in time A of an enzymatic reaction in the electrochemical measurement illustrated in FIG. 1.

First, according to the process illustrated in FIG. 1, current values when the time A from the start of an enzymatic reaction to voltage application is 3 seconds and the time B from the voltage application to acquisition of the current values was 0.1 seconds and current values when the time A is 20 seconds and the time B is 0.1 seconds were calculated. The results are illustrated in FIG. 2. As illustrated in FIG. 2, the difference in time A from the start of the enzymatic reaction to the voltage application appeared as a difference in the current values. Note that in FIG. 2, the position of the electrode located immediately below the EB is y=0 $\mu$m and current values from the electrode located immediately below the EB and the six electrodes located on both side are plotted (the same applies to graphs in FIGS. 8 to 11, which will be described later).

The present invention performs a measurement target elimination step of eliminating a measurement target by providing a measurement target eliminating electrode in an electrolytic solution and applying a eliminating voltage of the same polarity as a measuring voltage between the measurement target eliminating electrode and a counter electrode to oxidize or reduce a measurement target, a measurement target diffusion step of diffusing a new measurement target after stopping the application of the eliminating voltage, and an electrochemical measurement step of measuring a current by applying the measuring voltage between a working electrode and the counter electrode after diffusing the new measurement target. Three forms of the measurement target eliminating electrodes (forms 1 to 3) used in the numerical analysis will be described below.

Figure 3:
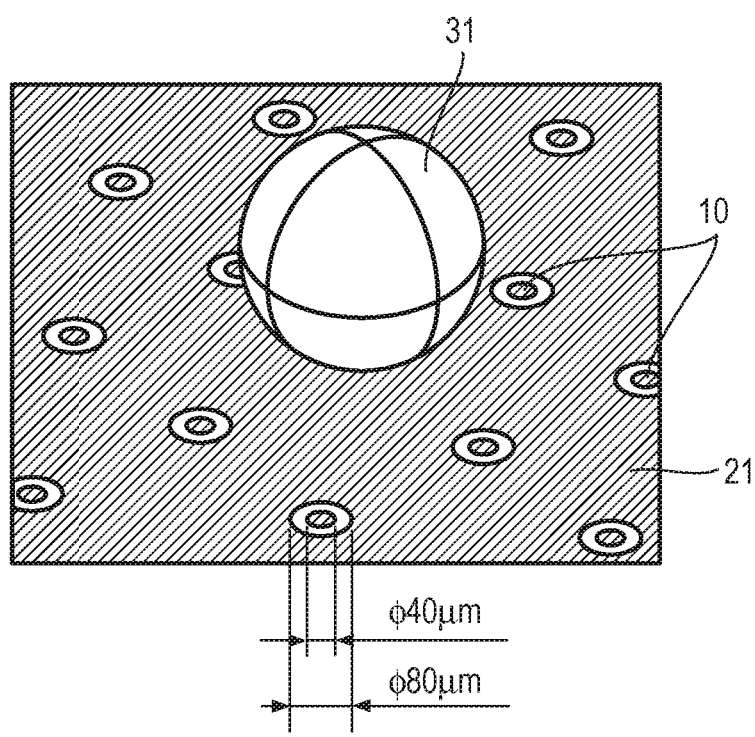
FIG. 3 is a perspective view of a first example measurement target eliminating electrode in the present invention.
Figure 4:
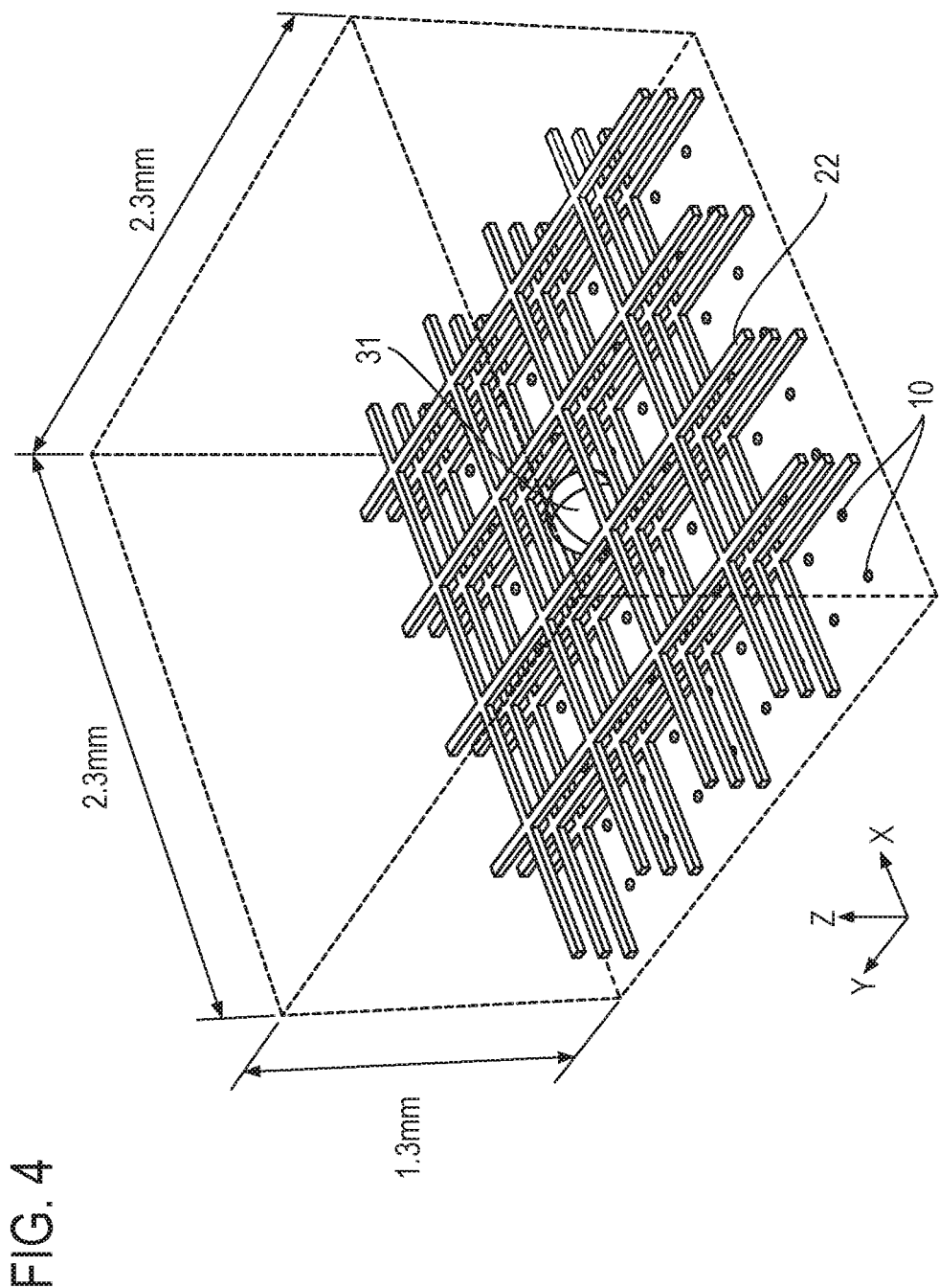
FIG. 4 is a perspective view of a second example measurement target eliminating electrode in the present invention.
Figure 5:
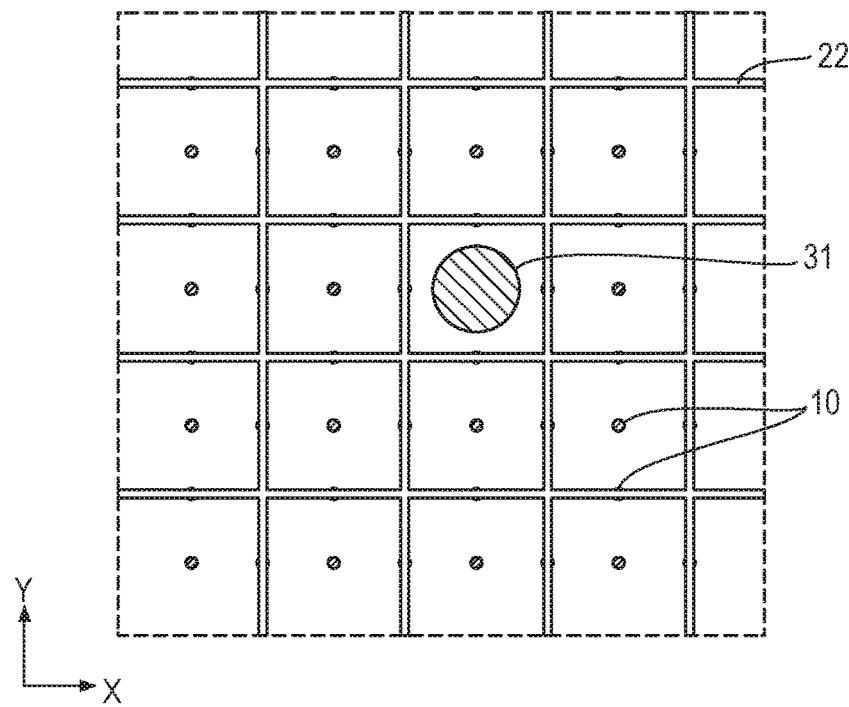
FIG. 5 is a plan view of the measurement target eliminating electrode illustrated in FIG. 4.
Figure 6A:
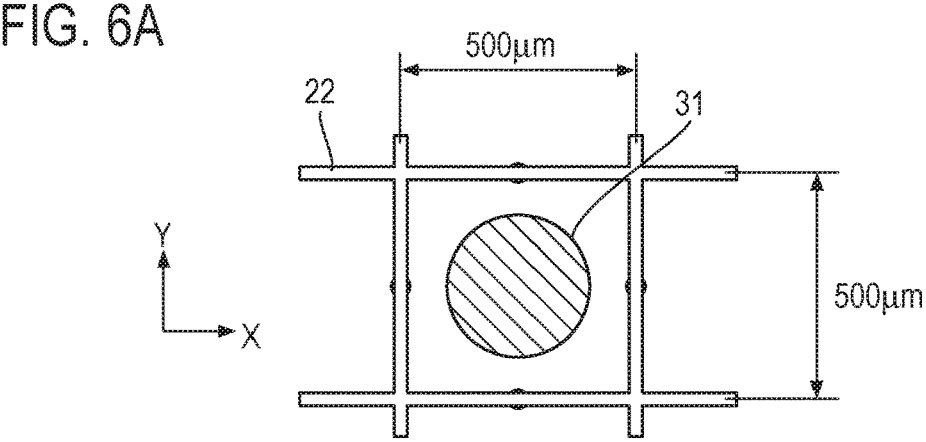
FIG. 6A is a partial enlarged view of a part of FIG. 5 from which some elements are omitted and FIG. 6B is a front view corresponding to FIG. 6A and illustrating the part without omission.
Figure 6B:
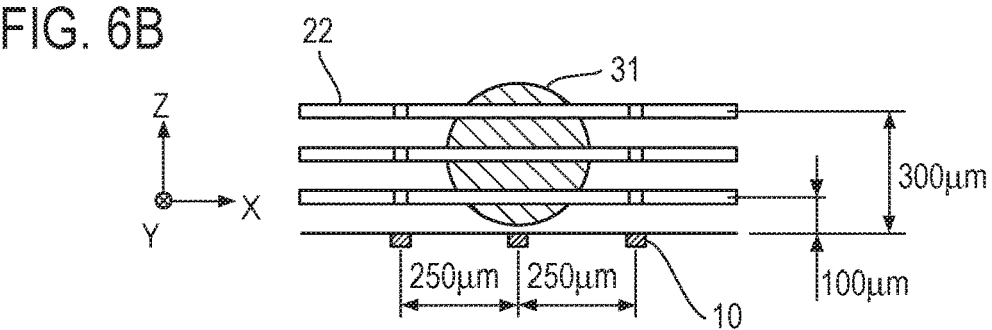

Form 1: A measurement target eliminating electrode having the same polarity as working electrodes are provided in the same plane as the working electrodes. The measurement target eliminating electrode is disposed so as to completely cover the entire surface around the working electrodes with gaps that prevent, electric conduction with the working electrodes. FIG. 3 illustrates the measurement target eliminating electrode. The measurement target eliminating electrode 21 is disposed so as to completely cover the entire surface around ϕ40-μm working electrodes 10 with a 20-μm concentric ring gap around each of the ϕ40-μm working electrodes. In FIG. 3, reference numeral 31 denotes a ϕ300-μm-diameter EB. The EB 31 is located immediately above a working electrode 10.

Form 2: A measurement target eliminating electrode in the form of three-dimensional grid that has the same polarity as working electrodes is disposed near the working electrodes. FIGS. 4, 5, 6A and 6B illustrate an arrangement and configuration of the measurement target eliminating electrode 22. Three two-dimensional grids extending along the XY directions are stacked in the Z direction to form the three-dimensional grid. Each grid is [a square symbol—there is no matching font] 30 μm thick with a pitch of 500 μm. The measurement target eliminating electrode 22 is disposed in the position illustrated in FIGS. 4, 5, 6A and 6B with respect to the working electrodes 10 with a pitch of 250 μm. Note that the distance between the three two-dimensional grids in the Z direction is 100 μm.

Form 3: Form 3 has a structure that is a combination of form 1 and form 2.

Voltage application to the measurement target eliminating electrode is reproduced by setting analytic boundary conditions so that the PAP concentration during voltage application becomes zero as with the working electrodes.

Figure 7:
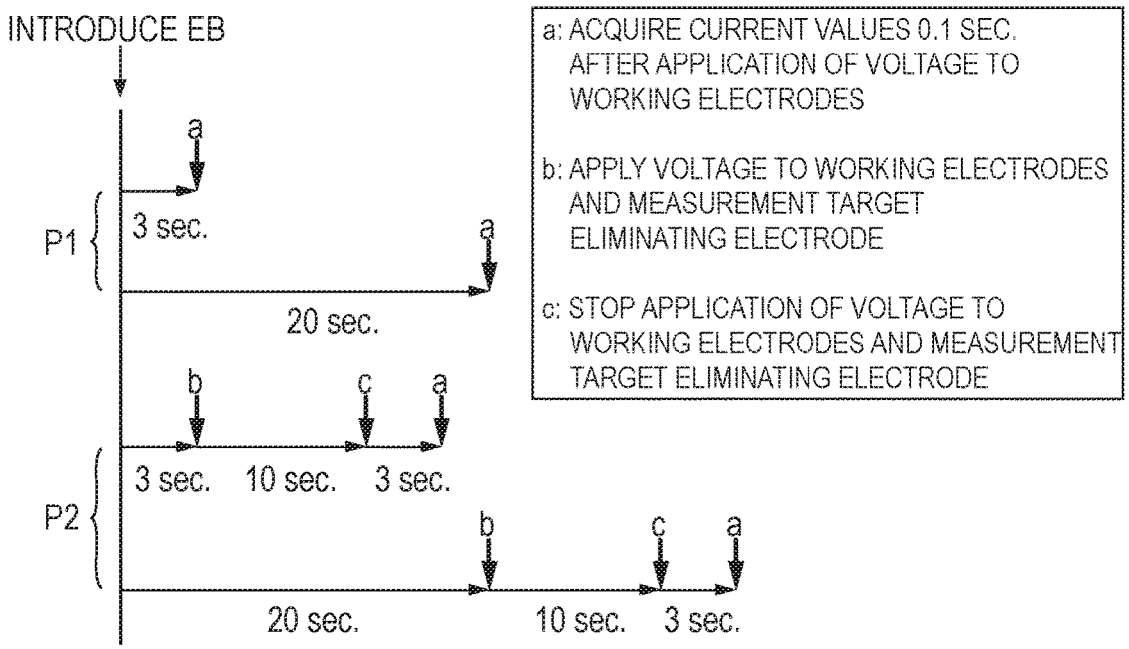
FIG. 7 is a chart illustrating a measurement process of electrochemical measurement according to the present invention together with a conventional measurement process.

P1 in FIG. 7 illustrates a process of producing the calculation results illustrated in FIG. 2 and P2 in FIG. 7 illustrates a process including the measurement target elimination step using a measurement target eliminating electrode, i.e. a process of the electrochemical measurement method according to the present invention.

It was assumed that the measurement target elimination step (PAP concentration distribution elimination step) was performed for 10 seconds by applying an eliminating voltage of the same polarity as a measuring voltage to the working electrodes and the measurement target eliminating electrode in a state 3 seconds after the start of an enzymatic reaction and in a state 20 seconds thereafter, then the application of the eliminating voltage was stopped and the measurement target diffusion step of causing an enzymatic reaction again for 3 seconds and diffusing a new measurement target was performed, thereafter the measuring voltage was applied to the working electrodes, and the electrochemical measurement step was performed. On this assumption, current values 0.1 seconds after were calculated.

Figure 8:
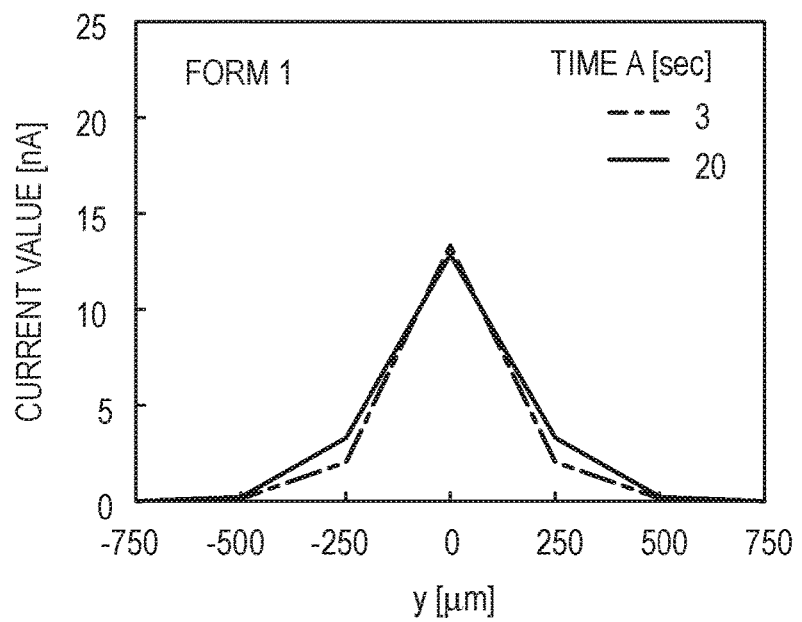
FIG. 8 is a graph illustrating current values calculated by performing a measurement target elimination step using the first example measurement target eliminating electrode.
Figure 9:
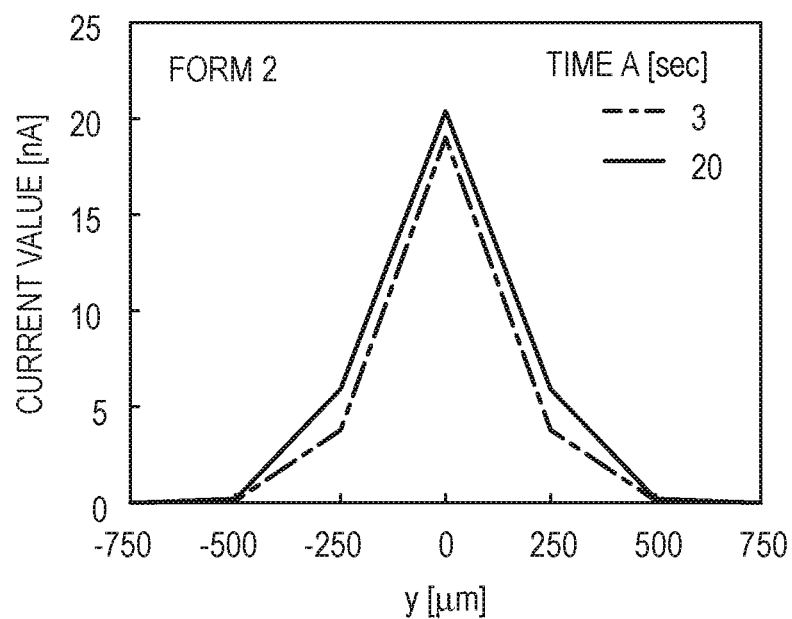
FIG. 9 is a graph illustrating current values calculated by performing the measurement target elimination step using the second example measurement target eliminating electrode.
Figure 10:
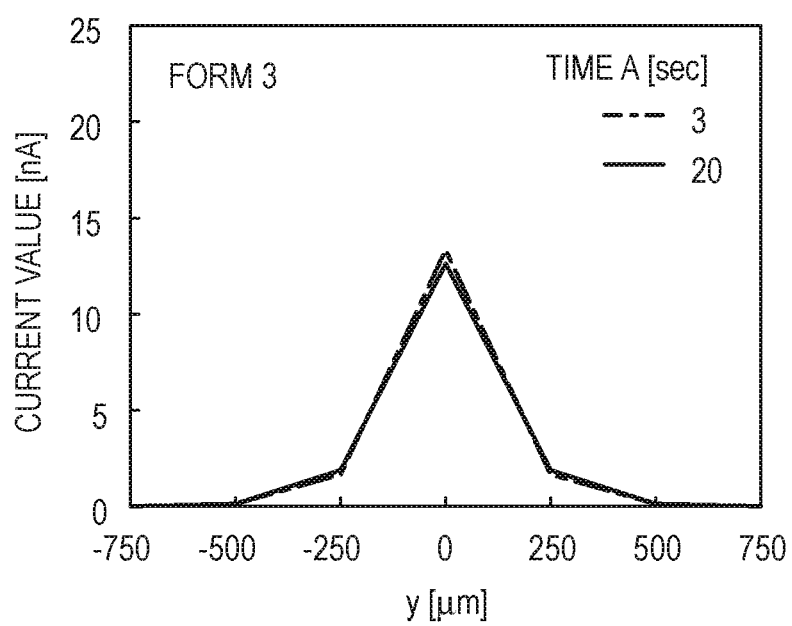
FIG. 10 is a graph illustrating current values calculated by performing the measurement target elimination step using a third example measurement target eliminating electrode.

FIGS. 8, 9 and 10 illustrate calculated current values for measurement target eliminating electrodes in form 1, form 2 and form 3, respectively.

Since the reaction (production and diffusion of the measurement target . . . the measurement target diffusion step) after the measurement target elimination step is invariable regardless of whether the period of time before the measurement target elimination step is 3 seconds or 20 seconds, it is desirable that the results for both of the case where the period of time before the measurement target elimination step is 3 seconds and the case where the period of time is 20 seconds be identical. The results for 3 seconds and 20 seconds for forms 1, 2 and 3 are more sufficiently close to each other than the results illustrated in FIG. 2.

When there is convection in an electrolytic solution, for example, the flow of the electrolytic solution can disturb the PAP concentration distribution formed by an EB and can influence measurement. Regarding this, results of calculation on effects of the electrochemical measurement method according to the present invention in the case where there is convection in an electrolytic solution will be described.

Calculations were performed for the following three cases (cases 1 to 3).

Case 1: Current values 0.1 seconds after voltage application where the time from the start of an enzymatic reaction to the voltage application is 10 seconds.

Case 2: Current values 0.1 seconds after voltage application where the time from the start of an enzymatic reaction to the voltage application is 10 seconds and there is convection with a velocity of 50 μm/s in the direction parallel to an array of working electrodes (the Y direction) at the start of the enzymatic reaction.

Case 3: Current values 0.1 seconds after voltage application where there is convection with a velocity of 50 μm/s in the direction parallel to the array of working electrodes (the Y direction) at the start of an enzymatic reaction, the measurement target elimination step is performed for 10 seconds using working electrodes and a measurement eliminating electrode having the same polarity as the working electrodes after 10 seconds convection, then the application of the eliminating voltage is stopped, an enzymatic reaction is caused again, the measurement target diffusion step is performed for 10 seconds, and then the voltage is applied to the working electrodes.

Figure 11:
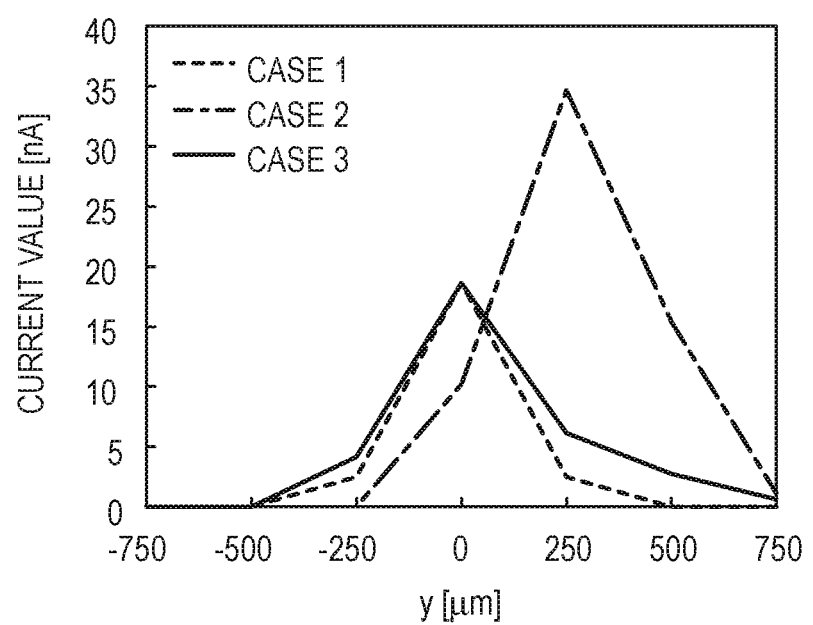
FIG. 11 is a graph illustrating a difference between current values calculated with and without performing the measurement target elimination step in the case where there is convection.

FIG. 11 illustrates results of the calculations of current values in cases 1 to 3. It can be seen that when the measurement target elimination step is not performed, the results are distorted by convection as in case 2 and the peak current value is at a position deviated from where the peak should be (the position in which the EB is located), whereas in case 3 in which the measurement target elimination step is performed, a current value close to the current value in case 1 which should be acquired can be acquired, thus influences of convection and liquid fluctuations can be eliminated.

The results of the numerical analysis performed have been described above. By performing the measurement target elimination step as described above in electrochemical measurement in which working electrodes that supply and receive electrons to and from a measurement target to cause an oxidation-reduction reaction and a counter electrode connected to the working electrodes through an external power source are provided in an electrolytic solution containing the measurement target and a measuring voltage is applied between the working electrodes and the counter electrode to measure a current flowing between the working electrodes and the counter electrode in proportion to the amount of the measurement target, the measurement target that exists at least in a range in the electrolytic solution that influences the measurement are entirely eliminated by being oxidized or reduced and the process of production and diffusion thereof is initialized and the state in the electrolytic solution is reset. Accordingly, conditions of production and diffusion of the measurement target can be made uniform among iterations of measurement and among samples measured at a time and therefore measurement conditions can be made uniform by controlling and keeping the duration of the subsequent measurement target diffusion step constant.

Further, by performing the measurement target elimination step in this way, influences of liquid fluctuations and convection of electrolytic solution can be avoided and, in addition, measurement can be performed at a timing desired by a measurer after introduction of samples (biometric specimens) that produce a measurement target.

Note that though the measurement target elimination step is performed by applying an eliminating voltage to both of a measurement target eliminating electrode and working electrodes in the method described above, the measurement target elimination step may be performed by applying the eliminating voltage only to the measurement target eliminating electrode, for example.

Figure 12:
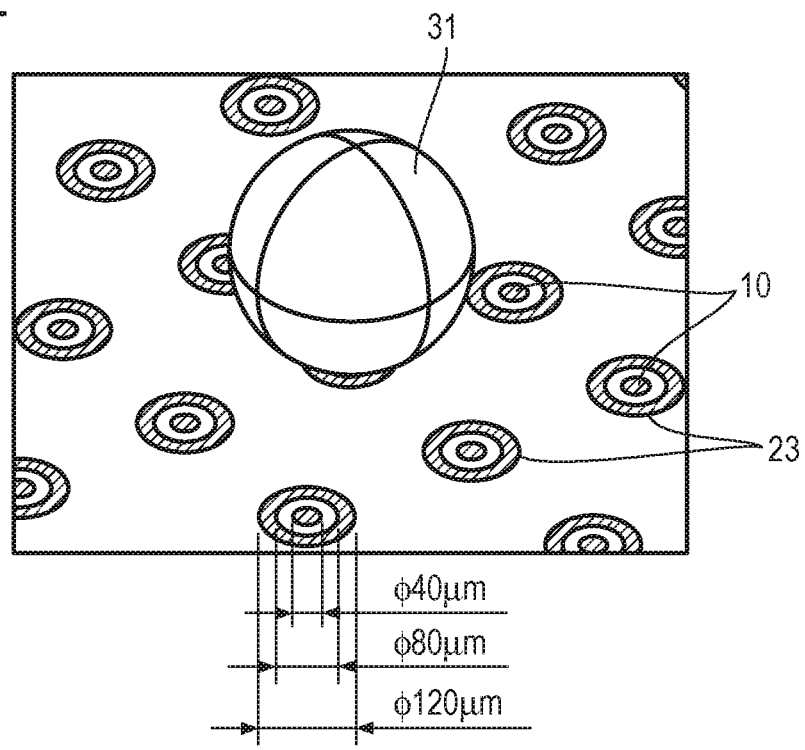
FIG. 12 is a perspective view of a fourth example measurement target eliminating electrode in the present invention.
Figure 13:
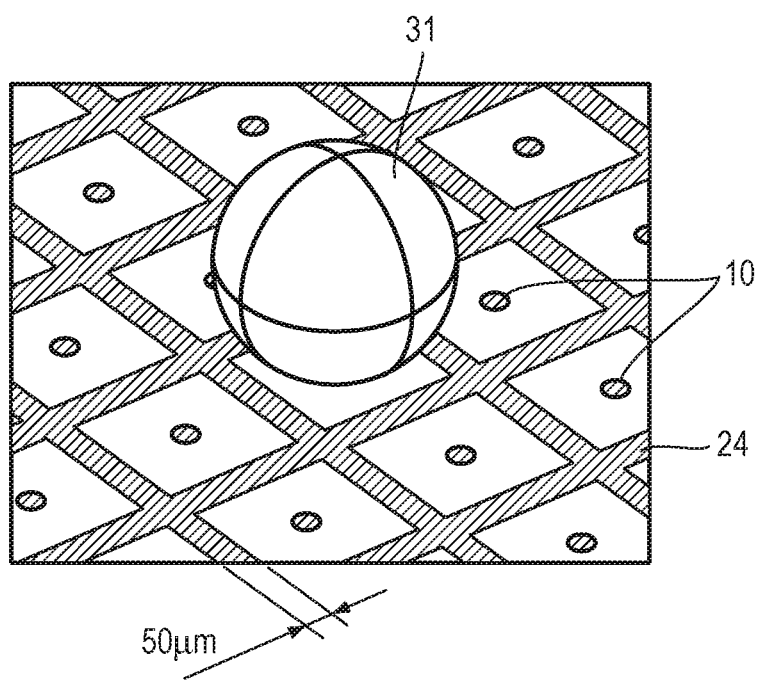
FIG. 13 is a perspective view of a fifth example measurement target eliminating electrode according to the present invention.

Forms of measurement target eliminating electrodes are not limited to those described above. For example, forms as illustrated in FIGS. 12 and 13 may be employed. In FIG. 12, each measurement target eliminating electrode 23 is in the form of a ring, provided in the same plane as working electrodes 10 and disposed around a working electrode 10 with φ40 μm. Each ring-like measurement target eliminating electrode 23 has an outer diameter of φ120 μm, for example, and an inner diameter of φ80 μm, for example.

FIG. 13 illustrates a measurement target eliminating electrode formed in a two-dimensional grid pattern. The measurement target eliminating electrode 24 is provided in the same plane as working electrodes 10, and is disposed around each working electrode 10 to surround the working electrode 10. The grid in this example is 50 μm wide with a pitch of 250 μm.

Measurement target eliminating electrodes may have form 2 (the three-dimensional grid) illustrated in FIGS. 4, 5, 6A and 6B described above in combination with the forms illustrated in FIGS. 12 and 13. Note that when biological specimens that produce measurement targets are small, measurement target eliminating electrodes provided only on the same plane as working electrodes may achieve the effects.

Further, measurement target eliminating electrodes that have a three-dimensionally extending form different from the form 2 (the three-dimensional grid) may be fabricated. For example, holes or recesses for placing biological specimens inside them may be provided in a mass of gold fibers aggregated in a steel-wool form and the mass of the gold fibers may be supported or suspended above working electrodes in such a way that the gold fibers do not contact the working electrodes. Alternatively, a porous material that has an appropriate porosity and is plated with gold may be used.

A configuration of an electrochemical measurement device according to the present invention will be described next.

Figure 14:
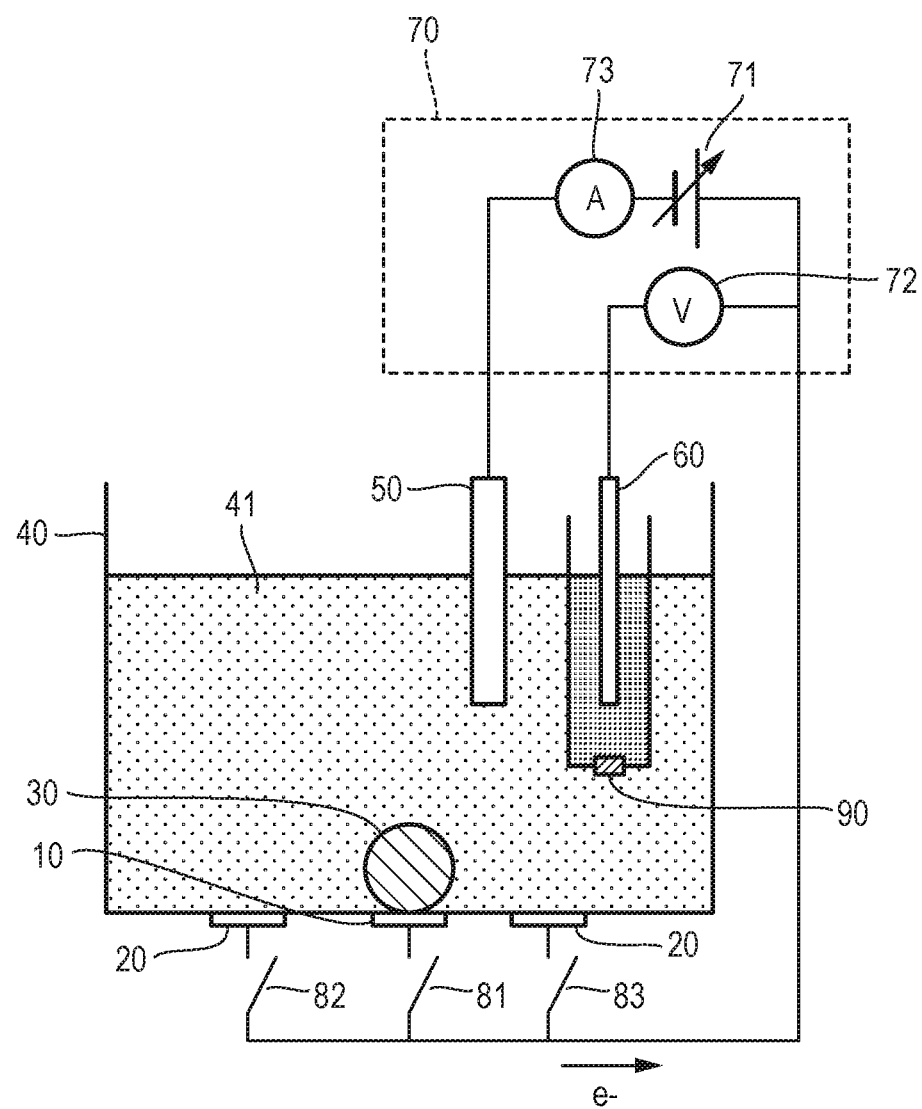
FIG. 14 is a diagram for explaining a configuration of one example embodiment of an electrochemical measurement device according to the present invention.

FIG. 14 schematically illustrates a configuration of the electrochemical measurement device. The electrochemical measurement device includes an electrolytic solution well 40 designed to contain an electrolytic solution 41 and a biological specimen 30 that produces a measurement target in the electrolytic solution 41. Working electrodes 10, measurement target eliminating electrodes 20, a counter electrode 50 and a reference electrode 60 are provided in the electrolytic solution well 40. While the working electrodes 10 and the measurement target eliminating electrodes 20 are schematically depicted in FIG. 14, many working electrodes 10 are arranged in an array with a predetermined pitch as described previously and the measurement target eliminating electrodes 20 have any of the configurations of the measurement target eliminating electrode 21 illustrated in FIG. 3, the measurement target eliminating electrode 22 illustrated in FIGS. 4, 5, 6A and 6B, the measurement target eliminating electrode 23 illustrated in FIG. 12, and the measurement target eliminating electrode 24 illustrated in FIG. 13, or have a configuration in which any of the measurement target eliminating electrodes 21, 23, and 24 are used in combination with the measurement target eliminating electrode 22. Reference numeral 90 in FIG. 14 indicates a salt bridge.

The working electrodes 10, the measurement target eliminating electrodes 20, the counter electrode 50, and the reference electrode 60 in this example are connected to a potentiostat 70 as illustrated in FIG. 14. The potentiostat 70 includes a variable power source 71, a voltmeter 72 and an ammeter 73. A measuring voltage is applied between the working electrodes 10 and the counter electrode 50 by the potentiostat 70 and an interelectrode current that flows between the working electrode 10 and the counter electrode 50 in proportion to the amount of a measurement target while the measuring voltage is being applied is measured by the potentiostat 70.

Further, when the measuring voltage is not applied between the working electrode 10 and the counter electrode 50, an eliminating voltage that has the same polarity as the measuring voltage is applied between the measurement target eliminating electrodes 20 and the counter electrode 50 by the potentiostat 70. Application of the measuring voltage to the working electrode 10 is accomplished by turning on a switch 81 and turning off switches 82 and 83; application of the eliminating voltage to the measurement target eliminating electrodes 20 is accomplished by turning on the switches 82 and 83 and turning off the switch 81. Note that the eliminating voltage may also be applied to the working electrode 10 by turning on the switch 81.

Though the eliminating voltage is applied from the potentiostat 70 to the measurement target eliminating electrodes 20 in FIG. 14, application of the eliminating voltage is not so limited and the eliminating voltage may be applied using a power source separate from the potentiostat 70.

A configuration of a transducer according to the present invention that is used for electrochemical measurement of a measurement target generated from a biological specimen will be described next with reference to FIGS. 15A, 15B and 16.

The transducer is called Bio-LSI chip, in which an electrolytic solution well 40 that can contain an electrolytic solution 41 and a biological specimen immersed in the electrolytic solution 41 is mounted on an LSI chip 100. A hole 42 is formed in the center of the electrolytic solution well 40 and the LSI chip 100 is disposed on the bottom end of the hole 42 in such a way that the LSI chip 100 covers the hole 42.

The LSI chip 100 and the electrolytic solution well 40 is mounted and fixed on a substrate 110 and a pattern 111 of many conductors for connection with an external device that controls the transducer is formed on the substrate 110. Reference numeral 120 in FIG. 15B indicates bonding wires that interconnect the LSI chip 100 and the pattern 111 of conductors.

A sensor region 101 is formed on the top surface of the LSI chip 100. In FIG. 15A, the sensor region 101 is indicated by hatching and is defined in the position of the hole 42 in the bottom surface of the electrolytic solution well 40. While details are omitted from the figure, 20×20=400 working electrodes (first electrodes) of φ40 μm are formed in an array with a pitch of 250 μm in the sensor region 101 in this example. Further, measurement target eliminating electrodes (second electrodes) are formed in such a way that each of the measurement target eliminating electrodes is positioned in the same plane as the working electrodes and around each working electrode. The measurement target eliminating electrodes have any of the configurations of the measurement target eliminating electrodes 21, 23 and 24 illustrated in FIGS. 3, 12 and 13, respectively.

The LSI chip 100 includes functions such as the function of applying a voltage to each of the working electrodes and the measurement target eliminating electrodes, the function of detecting a reaction at each working electrode as a current value and amplifying the current value, and the function of switching. The working electrodes and the measurement target eliminating electrodes are formed by a liftoff method, for example.

Figure 15A:
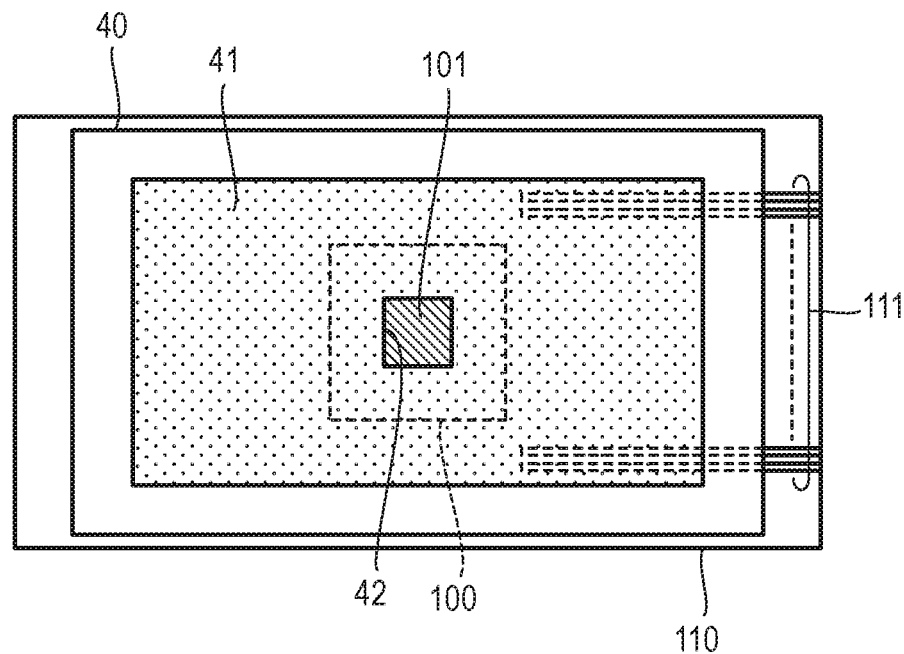
FIG. 15A is a plan view illustrating one example embodiment of a transducer according to the present invention and FIG. 15B is a cross-sectional view of the transducer illustrated in FIG. 15A.
Figure 15B:
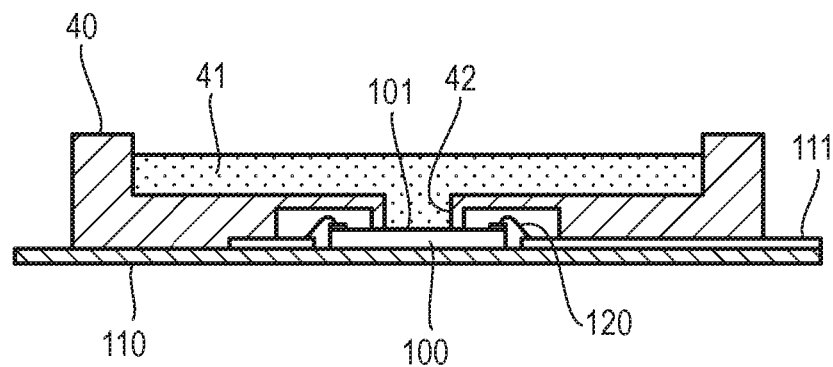
Figure 16:
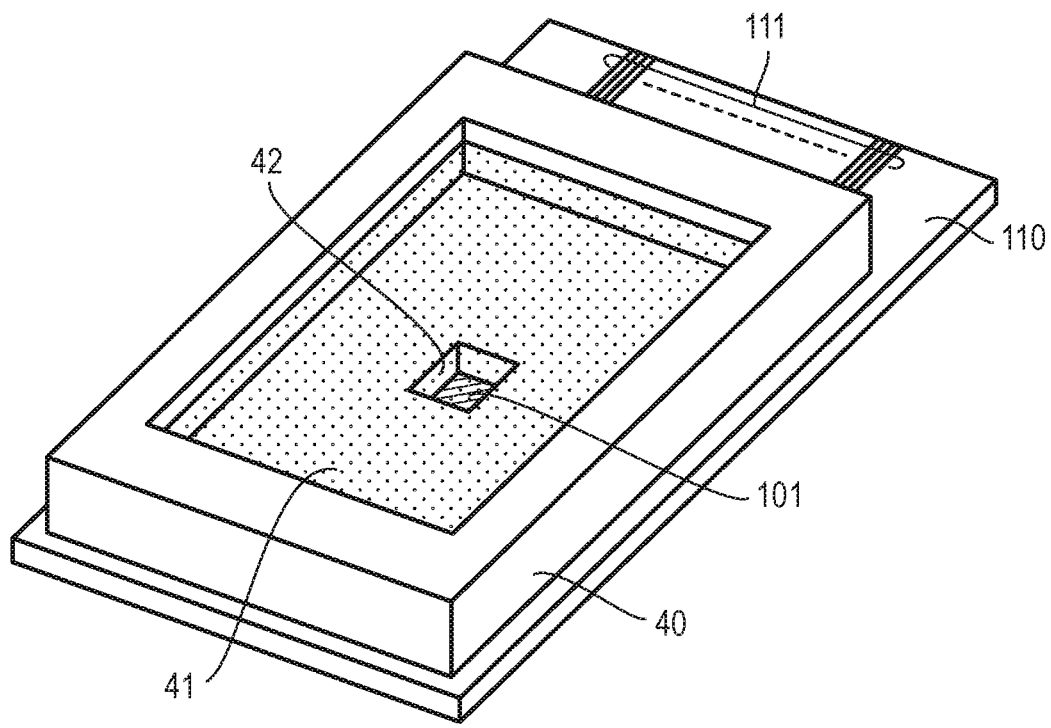
FIG. 16 is a perspective view of the transducer illustrated in FIG. 15A.

While the transducer illustrated in FIGS. 15A, 15B and 16 includes the measurement target eliminating electrodes in the same plane as the working electrodes, the transducer may further include measurement target eliminating electrodes having a three-dimensional grid structure as illustrated in FIGS. 4, 5, 6A and 6B described above.

Figure 17A:
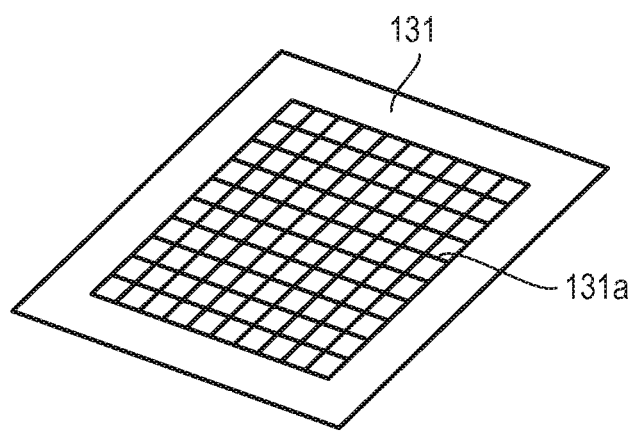
FIG. 17A is a perspective view illustrating a specific form of a component for forming the measurement target eliminating electrode illustrated in FIG. 4
Figure 17B:
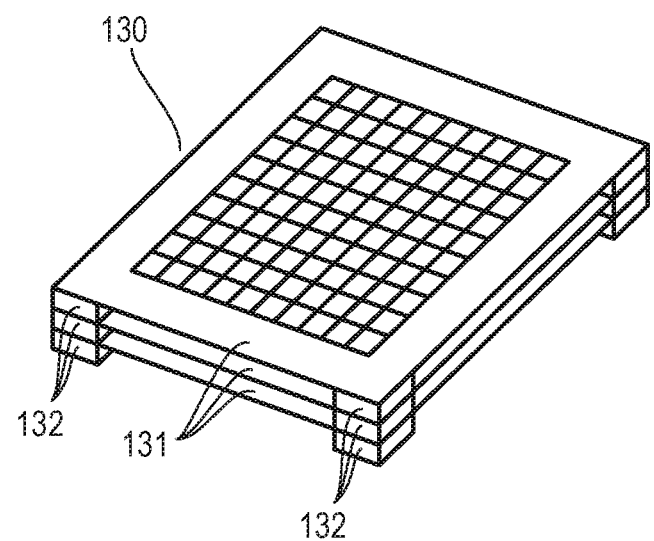
FIG. 17B is a perspective view of the measurement target eliminating electrode formed by using the component illustrated in FIG. 17A.
Figure 18:
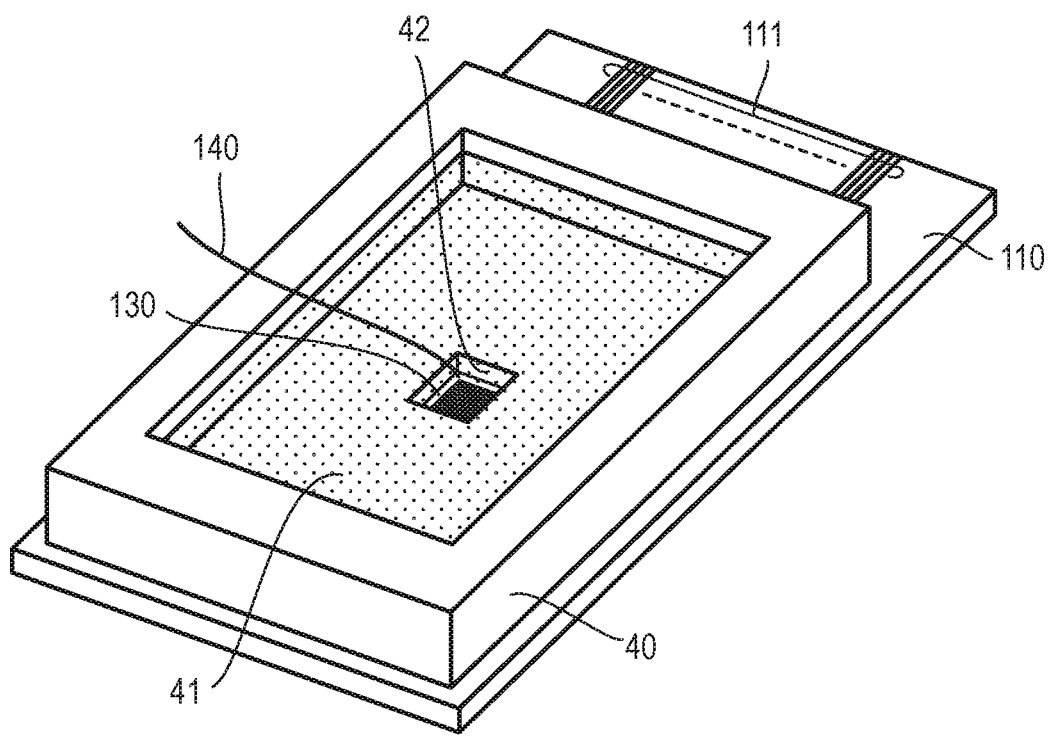
FIG. 18 is a perspective view of a transducer in which the measurement target eliminating electrode illustrated in FIG. 17B is incorporated.

FIGS. 17A and 17B illustrates a specific configuration of a measurement target eliminating electrode (third electrode) which has a three-dimensional grid structure and is to be provided in a transducer, and FIG. 18 illustrates a transducer as illustrated in FIGS. 15A, 15B and 16 to which the measurement target eliminating electrode having the three-dimensional grid structure is added.

The measurement target eliminating electrode 130 having the three-dimensional grid structure in this example is made up of three metal plates 131 and a total of 12 spacers 132. The metal plates 131 are made of copper or nickel and is approximately 30 µm thick. A mesh 131a is formed in each of the metal plates 131 as illustrated in FIG. 17A by processing such as photolithography and etching. The line/space (L/S) of the mesh 131a is 30 µm/470 µm. The spacers 132 are disposed at the four corners of the metal plate 131 in which the mesh 131a is formed and the three such metal plates 131 are stacked with the spacers 132 between them to form the measurement target eliminating electrode 130 having a three-dimensional grid structure as illustrated in FIG. 17B. Each spacer 132 is 70 µm thick and, with the spacers 132, the metal plates 131 in which the meshes 131a are formed are stacked with a gap of 100 µm between them. The spacers 132 and the metal plates 131 are fixed to one another by spot welding or otherwise and after being stacked, plated with gold to complete the measurement target eliminating electrode 130 having the three-dimensional grid structure.

The measurement target eliminating electrode 130 having the three-dimensional grid structure is placed in the hole 42 and disposed above the sensor region 101 as illustrated in FIG. 18. Reference numeral 140 in FIG. 18 indicates a conductor to be connected to an external power source for applying an eliminating voltage to the measurement target eliminating electrode 130. Note that a configuration is also possible in which an eliminating voltage is applied from the sensor region 101 of the LSI chip 100 to the measurement target eliminating electrode 130.

A counter electrode and a reference electrode are provided as components separate from the transducer and are placed in an electrolytic solution 41 when measurements are performed (during use).

What is claimed is:

1. An electrochemical measurement method using an electrochemical measurement device that includes: an electrolytic solution well storing an electrolytic solution; a working electrode located in the electrolytic solution well; a counter electrode located in the electrolytic solution well; an eliminating electrode located in the electrolytic solution well; and a specimen contained in the electrolytic solution and generating target substance, the method comprising:
applying an eliminating voltage between the eliminating electrode and the counter electrode to eliminate the target substance by oxidizing or reducing the target substance;
diffusing newly-generated target substance by stopping the applying of the eliminating voltage; and
after the diffusing of the newly-generated target substance, applying a measuring voltage, which has the same polarity as the eliminating voltage, between the working electrode and the counter electrode to measure a current that flows between the working electrode and the counter electrode in proportion to the amount of the newly-generated target substance.

2. The electrochemical measurement method according to claim 1,
wherein in the applying of the eliminating voltage, the eliminating voltage is concurrently applied between the working electrode and the counter electrode.

3. The electrochemical measurement method according to claim 2,
wherein the eliminating electrode is located in the same plane as the working electrode.

4. The electrochemical measurement method according to claim 3,
wherein the eliminating electrode is ring shaped and is disposed around the working electrode.

5. The electrochemical measurement method according to claim 3,
wherein the eliminating electrode has a shape like a two-dimensional grid, and
the working electrode is positioned at one of interstices of the two-dimensional grid, without contacting the eliminating electrode.

6. The electrochemical measurement method according to claim 3,
wherein the eliminating electrode is a flat electrode in which voids are formed, and
the working electrode is positioned at one of the voids, without contacting the eliminating electrode.

7. The electrochemical measurement method according to claim 2,
wherein the eliminating electrode has a three-dimensionally extending structure.

8. The electrochemical measurement method according to claim 7,
wherein the eliminating electrode has a shape like a three-dimensional grid and is disposed above a surface in which the working electrode is located.

9. The electrochemical measurement method according to claim 2,
wherein the eliminating electrode includes both of an electrode located in the same plane as the working electrode and an electrode disposed above the plane and having a three-dimensionally extending structure.

10. The electrochemical measurement method according to claim 1,
wherein the eliminating electrode is located in the same plane as the working electrode.

11. The electrochemical measurement method according to claim 10, wherein the eliminating electrode is ring shaped and is disposed around the working electrode.

12. The electrochemical measurement method according to claim 10,
wherein the eliminating electrode has a shape like a two-dimensional grid, and
the working electrode is positioned at one of interstices of the two-dimensional grid, without contacting the eliminating electrode.

13. The electrochemical measurement method according to claim 10,
wherein the eliminating electrode is a flat electrode in which voids are formed, and
the working electrode is positioned at one of the voids, without contacting the eliminating electrode.

14. The electrochemical measurement method according to claim 1,
wherein the eliminating electrode has a three-dimensionally extending structure.

15. The electrochemical measurement method according to claim 14,
wherein the eliminating electrode has a shape like a three-dimensional grid and is disposed above a surface in which the working electrode is located.

16. The electrochemical measurement method according to claim 1,
wherein the eliminating electrode includes both of an electrode located in the same plane as the working electrode and an electrode disposed above the plane and having a three-dimensionally extending structure.

* * * * *